US009482215B2

(12) United States Patent
Werbner

(10) Patent No.: US 9,482,215 B2
(45) Date of Patent: Nov. 1, 2016

(54) LIQUID EXTRACTION SYSTEM WITH REDUCED EXPOSURE TO AIR

(71) Applicant: Norman Werbner Information Services, Inc., Long Key, FL (US)

(72) Inventor: Norman Werbner, Long Key, FL (US)

(73) Assignee: Norman Werbner Information Services, Inc., Long Key, FL (US)

( * ) Notice: Subject to any disclaimer, the term of this patent is extended or adjusted under 35 U.S.C. 154(b) by 367 days.

(21) Appl. No.: 13/946,181

(22) Filed: Jul. 19, 2013

(65) Prior Publication Data

US 2015/0020914 A1    Jan. 22, 2015

(51) Int. Cl.
| F04B 37/10 | (2006.01) |
| F04B 37/00 | (2006.01) |
| B67D 7/02 | (2010.01) |
| B01L 3/02 | (2006.01) |
| B67C 9/00 | (2006.01) |
| A61M 1/00 | (2006.01) |

(52) U.S. Cl.
CPC .............. *F04B 37/10* (2013.01); *F04B 37/00* (2013.01); *A61M 1/0068* (2014.02); *B01L 3/0231* (2013.01); *B67C 9/00* (2013.01); *B67D 7/0277* (2013.01)

(58) Field of Classification Search
CPC ............ B65D 81/245; B65D 83/0044; B67D 7/0277; B67D 7/0288; B01L 3/0231; B67C 9/00; A61M 1/0068; A61J 1/20; A61J 1/2089; F04B 37/00; F04B 37/10
USPC ............ 222/386; 422/501–526; 141/27, 319, 141/65; 604/403–416
See application file for complete search history.

(56) References Cited

U.S. PATENT DOCUMENTS

| 1,950,137 | A | | 3/1934 | Dowe |
| 2,393,217 | A | | 1/1946 | Brewton |
| 2,515,956 | A | | 7/1950 | Greenberg |
| 3,902,491 | A | | 9/1975 | Lajus |
| 3,987,941 | A | | 10/1976 | Blessing |
| 4,036,064 | A | * | 7/1977 | Hydo .................. G01N 35/0095 422/927 |
| 4,116,366 | A | | 9/1978 | Takenakashima et al. |
| 4,119,244 | A | | 10/1978 | Funke |
| 4,240,570 | A | | 12/1980 | Brown et al. |
| 4,616,514 | A | * | 10/1986 | Magnussen, Jr. ..... B01L 3/0227 403/369 |
| 4,691,842 | A | | 9/1987 | Foures |
| 5,299,408 | A | * | 4/1994 | Dupont ..................... B67B 1/04 53/109 |
| 5,454,268 | A | * | 10/1995 | Kim ...................... B01L 3/0231 422/505 |
| 5,770,158 | A | | 6/1998 | Eischen et al. |
| 5,770,160 | A | * | 6/1998 | Smith ................... B01L 3/0217 422/525 |

(Continued)

FOREIGN PATENT DOCUMENTS

FR    2066691 A5 *  8/1971 ............ B01L 3/0231

OTHER PUBLICATIONS

Wine Pipette for Sampling Wine, www.homebrewwest.ie/wine-pipette-for-sampling-wine-1239-p.asp, published Feb. 22, 2011, accessed Nov. 25, 2015.*

(Continued)

*Primary Examiner* — Mark A Laurenzi
*Assistant Examiner* — Andrew StClair
(74) *Attorney, Agent, or Firm* — Hovey Williams LLP

(57) ABSTRACT

A liquid extraction apparatus and a method of extracting a liquid from a container and storing the liquid are disclosed. The method includes inserting a liquid extraction member into a container and creating a pressure differential to cause the liquid to flow into a storage vessel.

20 Claims, 5 Drawing Sheets

(56) References Cited

U.S. PATENT DOCUMENTS

| | | | |
|---|---|---|---|
| 5,873,861 A | 2/1999 | Hitchins et al. | |
| 6,105,803 A | 8/2000 | Standish | |
| 6,168,761 B1* | 1/2001 | Kelly | B01L 3/0275 422/522 |
| 6,170,715 B1 | 1/2001 | Evans | |
| 6,290,105 B1 | 9/2001 | Cosentino | |
| 6,352,673 B1* | 3/2002 | Rainin | B01L 3/0217 422/525 |
| 6,365,110 B1* | 4/2002 | Rainin | B01L 3/0224 422/522 |
| 7,051,901 B2 | 5/2006 | Hickert | |
| 7,815,865 B2* | 10/2010 | Hoffman | B01L 3/0293 222/181.1 |
| 8,261,781 B2* | 9/2012 | Imai | A61M 5/31501 141/27 |
| 2002/0088827 A1 | 7/2002 | Colucci | |
| 2007/0039977 A1 | 2/2007 | Donaldson | |
| 2007/0119875 A1 | 5/2007 | Ehret et al. | |
| 2007/0138212 A1 | 6/2007 | Greenbaum | |
| 2007/0164058 A1 | 7/2007 | Burkovskiy | |
| 2008/0110847 A1 | 5/2008 | Rees et al. | |
| 2009/0081772 A1* | 3/2009 | Cayre | B01L 3/502 435/306.1 |
| 2011/0039329 A1* | 2/2011 | Gandy | A61M 1/0009 435/325 |
| 2011/0088493 A1* | 4/2011 | Blumentritt | B01L 3/0217 73/864.17 |
| 2011/0290826 A1 | 12/2011 | Harris | |
| 2012/0241476 A1 | 9/2012 | Lambrecht | |
| 2014/0001215 A1* | 1/2014 | Leckebusch | B01L 3/0217 222/386 |

OTHER PUBLICATIONS

Search Report and Written Opinion dated May 15, 2015 for corresponding PCT Patent Application No. PCT/US2014/047226; 12 pages.
Analytical Columns . . . Chromatography Specialists from the following webpage: http://www.analyticalcolumns.com/syringes/sge/sgesyringesmicrovol0.5-5.html; Printed on Jul. 19, 2013; 3 pages.
Gastight Syringes from the following webpage: http://www.hamiltoncompany.com/products/syringes/c/794/; Hamilton Company; Printed on Jul. 19, 2013; 2 pages.
7000 Series Modified Microliter Syringe; Hamilton Company, Reno, Nevada; Document No. 69065(Rev. F); Jul. 2007; 3 pages.
Syringe Selection Guide; Hamilton Company, Reno, Nevada, 13 pages.

* cited by examiner

LIQUID EXTRACTION SYSTEM WITH REDUCED EXPOSURE TO AIR

FIELD OF THE INVENTION

The invention relates generally to the extraction of liquids from a container. More particularly, the invention relates to apparatuses and methods for extracting liquids from a container, and storing the liquids, while minimizing the exposure to an external environment.

BACKGROUND OF THE INVENTION

The shelf life and/or usefulness of certain liquids can deteriorate upon exposure to environmental components external to the container storing the liquid. For example, the shelf life of wine significantly decreases upon being exposed to ambient air by oxidizing chemicals in the wine, which can alter its taste and color. Other liquids that are stored in sealed containers can also be oxidized or otherwise affected by the air. Even if a liquid is protected while being extracted from a container, the act of dispensing that liquid can introduce air into the remaining liquid. Current liquid extraction and/or liquid preservation devices attempt to alleviate these problems in a variety of ways; however, some are difficult to operate and do not provide an adequate solution for dispensing liquid from a container without introducing excess air into the remaining liquid. Therefore, there is a need for a liquid extraction apparatus and method that can successfully extract and store liquid to increase its shelf life and/or usefulness.

SUMMARY OF THE INVENTION

In one embodiment of the present invention, an apparatus for extracting a liquid from a container having an opening is provided that includes a liquid extraction member having a length ($L_e$) of at least 2 inches, where one end of the extraction member includes a liquid extraction inlet, where the extraction member is configured for insertion through the opening of the container and for positioning of the extraction inlet below the surface of the liquid; a storage vessel defining a liquid storage inlet coupled in fluid flow communication with the extraction member, where the maximum internal diameter ($D_s$) of the storage vessel is greater than the maximum internal diameter ($D_e$) of the liquid extraction member; a shiftable plunger received in the storage vessel and operable to create a pressure differential between the storage inlet and the extraction inlet so as to draw the liquid from the container, through the extraction member, and into the storage vessel; and an air blocking member received in the extraction member and shiftable between an initial blocking position and a final extraction position, where the air blocking member presents a lowermost surface that moves through a total distance ($X_b$) as the air blocking member is shifted from the initial blocking position to the final extraction position, where the lowermost surface is positioned less than $0.25X_b$ from the extraction inlet when the air blocking member is in the initial blocking position.

In another embodiment of the present invention, a process for extracting a liquid from a container and storing the liquid is provided that includes the steps of (a) inserting a liquid extraction member having a length ($L_e$) of at least 2 inches into a container to a depth such that the liquid extraction inlet of the extraction member extends below the surface of the liquid received in the container; (b) creating a pressure differential between the extraction inlet and a storage inlet of a storage vessel to thereby cause at least a portion of the liquid to flow from the container, through the extraction member, and into the storage vessel, where the maximum internal diameter ($D_s$) of the storage vessel is greater than the maximum internal diameter ($D_e$) of the liquid extraction member; and (c) during at least a portion of step (b), shifting an air blocking member in the liquid extraction member from an initial blocking position to a final extraction position, where the air blocking member presents a lowermost surface that moves through a total distance ($X_b$) as the air blocking member is shifted from the initial blocking position to the final extraction position, where the lowermost surface is positioned less than $0.25X_b$ from the extraction inlet when the air blocking member is in the initial blocking position.

In yet another embodiment of the present invention, an apparatus for extracting a liquid from a container having an opening is provided that includes a liquid extraction member having a lower liquid extraction inlet and an upper liquid extraction outlet, where the extraction member is configured for insertion through the opening of the container and for positioning of the liquid extraction inlet below the surface of the liquid; a storage vessel defining a liquid storage inlet coupled in fluid flow communication with the upper liquid extraction outlet, wherein the maximum internal diameter ($D_s$) of the storage vessel is greater than the maximum internal diameter ($D_e$) of the liquid extraction member; a first differential pressure generation device coupled in fluid flow communication with the liquid extraction member and configured to draw the liquid through the lower liquid extraction inlet, into the extraction member, and up to a level at or above the upper liquid extraction outlet; and a second differential pressure generation device coupled in fluid flow communication with the storage vessel and configured to draw the liquid through the liquid extraction outlet and into the storage vessel.

In another embodiment of the present invention, a process for extracting a liquid from a container and storing said liquid is provided that includes the steps of (a) inserting a liquid extraction member into a container to a depth such that a liquid extraction inlet of the extraction member extends below the surface of the liquid in the container; (b) creating a pressure differential between the extraction inlet and an upper portion of the liquid extraction member to thereby cause at least a portion of the liquid to flow from the container up into the upper portion of the liquid extraction member, where the maximum internal diameter ($D_s$) of the storage vessel is greater than the maximum internal diameter ($D_e$) of the liquid extraction member; and (c) creating a pressure differential between an extraction outlet in the upper portion of the liquid extraction member and the interior of a storage vessel to thereby cause at least a portion of the liquid to flow from the extraction member, through the extraction outlet, and into the storage vessel, where separate devices are used to create the pressure differentials of step (b) and step (c).

BRIEF DESCRIPTION OF THE FIGURES

Embodiments of the present invention are described herein with reference to the following drawing figures, wherein.

DETAILED DESCRIPTION

The following detailed description of the invention references various embodiments. The embodiments are intended to describe aspects of the invention in sufficient detail to enable those skilled in the art to practice the invention. Other embodiments can be utilized and changes can be made without departing from the scope of the present invention. Further, it should be understood that the below described embodiments are not exclusive of one another, and any portion of the description, properties, and parameters of any one embodiment can be combined with any portion of the description, properties, and parameters of any other embodiment. The following detailed description is, therefore, not to be taken in a limiting sense. The scope of the present invention is defined only by the appended claims, along with the full scope of equivalents to which such claims are entitled.

Figure 1A:
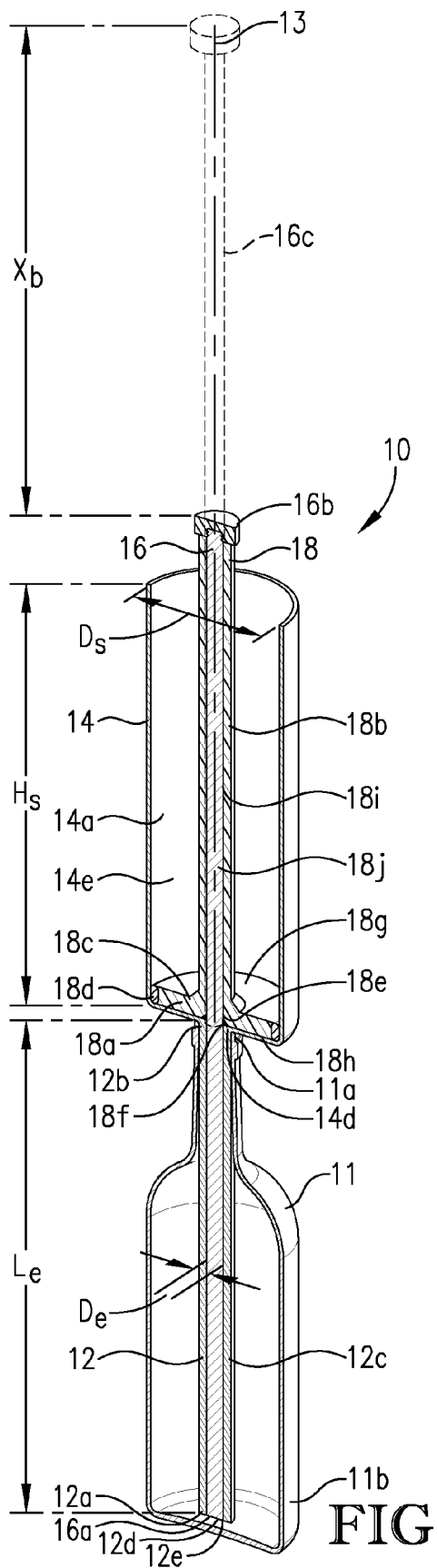
FIG. 1a is a perspective and cross-sectional view of a liquid extraction apparatus in accordance with one embodiment of the present invention, particularly illustrating a liquid extraction member partly received inside a container, a shiftable plunger partly received inside a storage vessel located above the container, and an air blocking member received inside both the extraction member and the shiftable plunger.

FIG. 1a depicts one embodiment of a liquid extraction apparatus 10 in accordance with the present invention. It should be understood that FIG. 1a depicts just one embodiment of a liquid extraction apparatus, and that a wide variety of embodiments of liquid extraction apparatuses are contemplated by the present invention. The liquid extraction apparatus 10 of FIG. 1a will now be described in detail.

The liquid extraction apparatus 10 of FIG. 1a is capable of extracting a liquid from a container 11 having an opening 11a. The container 11 can be any container suitable to contain or store a liquid. In certain embodiments, the container 11 can be a container for storing perishable liquids. In one or more embodiments, the container 11 can be a wine bottle.

The liquid can be any liquid where it is desirable to extract that liquid from a container 11 with minimal to no contact with the external environment. In certain embodiments, the liquid can be a perishable consumable liquid, such as, for example, wine, juice, milk, or a medicament. In one or more embodiments, the container 11 can be a wine bottle, and the liquid can be wine. In certain other embodiments, the liquid can be a non-consumable liquid, such as, for example, industrial chemicals, or household chemicals.

The liquid extraction apparatus 10 of FIG. 1a includes a liquid extraction member 12, a storage vessel 14, an air blocking member 16, and a shiftable plunger 18. In certain embodiments, the liquid extraction member 12 can be made of any material that is suitable for contacting a specific liquid stored in the container 11, such as, for example, stainless steel, glass, or a plastic material. In one or more embodiments, the liquid extraction member 12 can be coated in a substance that is suitable for contacting a specific liquid stored in the container 11.

The liquid extraction member 12 can be any size and shape as long as a portion of the extraction member 12 can be inserted into a container 11 and be positioned below a liquid surface. In certain embodiments, the liquid extraction member 12 is cylindrical in shape. In the embodiment depicted in FIGS. 1a and 1b, the extraction member 12 defines an internal extraction chamber 12d having a total volume $V_e$. In one or more embodiments, the total volume $V_e$ can be at least 0.08 mL, 2 mL, 5 mL, 15 mL, or 25 mL, and/or not more than 100 mL, 80 mL, 60 mL, or 50 mL.

In certain embodiments, the extraction member 12 has a length $L_e$, extending from the top end 12b to the extraction inlet 12a, that is at least 2 inches, 4 inches, 6 inches, 8 inches, or 10 inches, and/or not more than 40 inches, 30 inches, 20 inches, or 15 inches. In one or more embodiments, the extraction member 12 has a maximum internal diameter $D_e$ that is at least 0.02 inches, 0.05 inches, 0.1 inches, 0.25 inches, 0.5 inches, 0.75 inches and/or not more than 4 inches, 3 inches, 2 inches, 1 inches, or 0.65 inches. It should be understood that the maximum internal diameter $D_e$ refers to the distance of a straight line extending from one point on the inner surface 12c to another point on the inner surface 12c passing through the center of the extraction member 12, and does not necessarily require the extraction member 12 to have a circular or cylindrical shape.

In certain embodiments, the extraction member 12 has an $L_e:D_e$ ratio of at least 2:1, 4:1, 6:1, or 8:1, and/or not more than 1000:1, 100:1, 40:1, 30:1, 20:1, or 15:1. In one or more embodiments, the maximum external diameter $ED_e$ of the extraction member 12 can have the same values and ranges as the maximum internal diameter $D_e$ dimensions and ratios (e.g., $D_e$ and $L_e:D_e$) of the extraction member 12 discussed above. Further, as discussed above with reference to $D_e$, the $ED_e$ does not necessarily require the extraction member 12 to have a circular or cylindrical shape.

In an embodiment not depicted in the figures, the extraction member 12 can be composed of more than one article. For example, the extraction member 12 can be composed of at least 2 portions that are attached to one another. In such embodiments, the two separate portions of the extraction member 12 can be removably coupled to one another so that after using the liquid extraction apparatus 10, a bottom portion of the extraction member 12 can be removed to allow for more compact storage and/or easier cleaning of the apparatus 10.

Returning now to FIG. 1a, the extraction member 12 is coupled to the storage vessel 14. In certain embodiments, the top end 12b of the extraction member 12 can be fixedly coupled to the storage vessel 14. For example, in the embodiment depicted in FIG. 1a, the storage vessel 14 and the extraction member 12 are made of one unitary article. As best observed in FIG. 1b, the top end 12b of the extraction member 12 is integral with the bottom end 14d of the storage vessel 14. The embodiment depicted in FIGS. 1a and 1b further shows that the bottom end 14d of the storage vessel 14 includes a liquid storage inlet 14c that is aligned with the internal extraction chamber 12d of the extraction member 12, and with the interior channel 18i of the shiftable plunger 18.

In one or more embodiments, the top end 12b of the extraction member 12 may be removably coupled to the storage vessel 14. For example, in one or more embodiments, the top end 12b of the extraction member 12 can be coupled to the storage vessel 14 by complimentary threaded portions. The extraction member 12 can be removably coupled to the storage vessel 14 in a variety of ways, and a particular method can be chosen by one skilled in the art. In certain other embodiments, the extraction member 12 is coupled to the storage vessel 14 at a position other than the top end 12b. In certain embodiments, after the liquid extraction apparatus 10 is used to extract liquid from the container 11, the entire extraction member 12 can be removed from the storage vessel 14, for example, to allow for more compact storage and/or easier cleaning.

The storage vessel 14 can be any size and shape, and a particular size and shape can be chosen by one skilled in the art. In certain embodiments, such as the embodiment depicted in FIGS. 1a and 1b, the storage vessel 14 has a cylindrical shape. The storage vessel 14 of FIGS. 1a and 1b defines an internal storage chamber 14e having a total volume $V_s$. In one or more embodiments, the total volume $V_s$ is at least 0.1 liters, 0.25 liters, or 0.4 liters, and/or not more than 5 liters, 4 liters, or 3 liters.

In one or more embodiments, the storage vessel 14 has a maximum height $H_s$ that is at least 3 inches, 5 inches, 7 inches, or 9 inches, and/or not more than 30 inches, 20 inches, 15 inches, 12 inches, or 8 inches. In certain embodiments, the storage vessel 14 has a maximal internal diameter $D_s$ that is at least 1 inch, 2 inches, 3 inches, or 4 inches, and/or not more than 20 inches, 15 inches, 10 inches, or 8 inches. It should be understood that the internal diameter $D_s$ refers to a straight line extending from one point on the internal surface 14a to another point on the internal surface 14a passing through the center of the storage vessel 14, and does not necessarily require the storage vessel 14 to have a circular or cylindrical shape. In certain embodiments, the maximum external diameter $ED_s$ of the storage vessel 14 can have any or all of the same values and ranges as the maximum internal diameter $D_s$ of the storage vessel 14, and as discussed above with reference to the $D_s$ value, the $ED_s$ value does not require the storage vessel 14 to have a circular or cylindrical shape. In certain embodiments, the maximum external diameter $ED_s$ is greater than the internal dimensions of the opening of a standard size wine bottle, e.g., greater than 16-20 mm. In one or more embodiments, the storage vessel 14 cannot fit inside a standard size wine bottle 11. In another embodiment, all or a portion of the storage vessel 14 can fit inside a standard size wine bottle 11.

In various embodiments, the liquid extraction apparatus 10 has a $D_s:D_e$ ratio of at least 1.25:1, 1.5:1, 2:1, or 3:1, and/or not more than 1,000:1, 500:1, 100:1, or 20:1. In certain embodiments, the liquid extraction apparatus 10 has an $L_e:H_s$ ratio of at least 0.25:1, 0.5:1, 0.75:1, or 1:1, and/or not more than 5:1, 4:1, 3:1, or 2:1.

In certain embodiments, where the storage vessel 14 defines an internal storage chamber 14e having a total volume $V_s$, and the extraction member 12 defines an internal extraction chamber 12d having a volume $V_e$, the liquid extraction apparatus 10 has a $V_s:V_e$ ratio of at least 2:1, 4:1, 6:1, 8:1, or 20:1 and/or not more than 50,000:1, 5,000:1, 500:1, 50:1, or 25:1.

In one or more embodiments, the ratio $A_e:A_s$ of the maximal cross-sectional area $A_e$ of the extraction member 12 to the maximal cross-sectional area $A_s$ of the storage vessel 14 is at least 1:1.5, 1:2, 1:3, or 1:4, and/or not more than 1:500, 1:100, 1:50, 1:30, or 1:20.

Figure 1B:
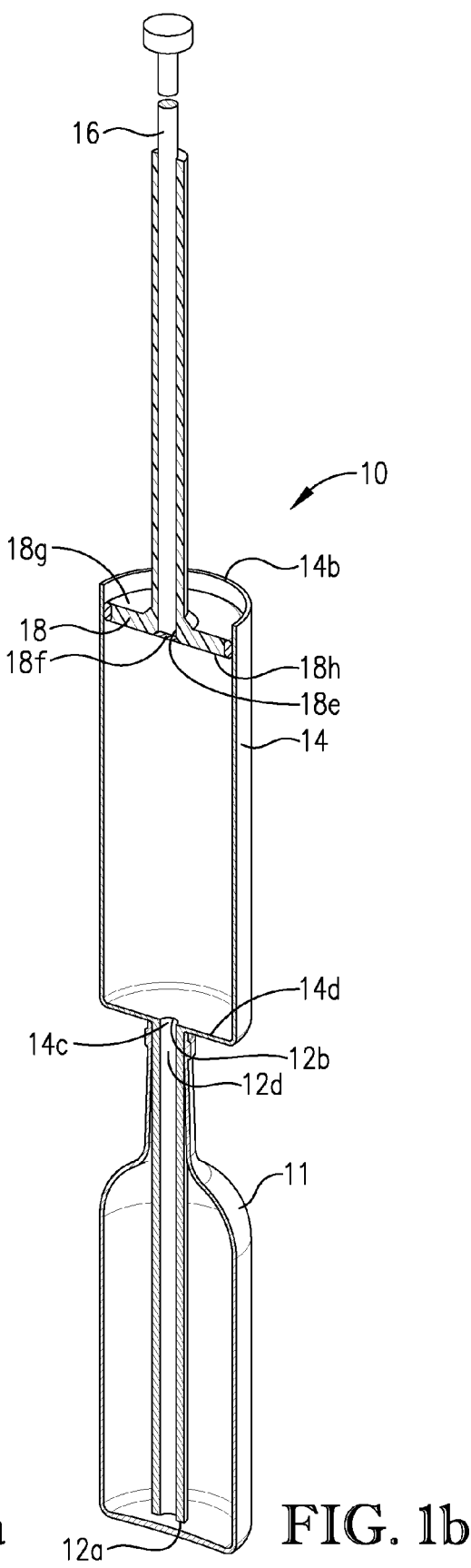
FIG. 1b is a perspective and cross-sectional view of the liquid extraction apparatus of FIG. 1a, particularly illustrating the lowermost surface of the air blocking member and the base portion of the shiftable plunger positioned near the top portion of the storage vessel.

In the embodiment depicted in FIGS. 1a and 1b, the liquid extraction apparatus 10 includes an air blocking member 16. In certain embodiments, the air blocking member 16 is received in the extraction member 12. In the embodiment depicted in FIGS. 1a and 1b, the liquid extraction apparatus 10 of FIG. 1a includes an air blocking member 16 received in the internal extraction chamber 12d of the extraction member 12, and in the interior channel 18i of the shiftable plunger 18.

The air blocking member 16 of FIGS. 1a and 1b can be any size and shape as long as it can block at least a portion of air from entering the extraction member 12. As used herein, the term air refers to air from the external environment. In one or more embodiments, the air blocking member 16 of FIGS. 1a and 1b can have a length $L_a$ of at least 2 inches, 5 inches, 7 inches, or 9 inches, and/or not more than 48 inches, 28 inches, 20 inches, or 12 inches.

In the embodiment depicted in FIGS. 1a and 1b, the air blocking member 16 has a substantially uniform thickness that contacts or nearly contacts the inner surface 12c of the extraction member 12 and the surface of the interior channel 18i of the shiftable plunger 18. In certain other embodiments, the air blocking member 16 does not have a substantially uniform thickness, but rather can have a narrower shaft having a lowermost surface that can contact the inner surface 12c of the extraction member 12 and/or the surface of the interior channel 18i of the shiftable plunger 18. For example, in such embodiments, the air blocking member 16 can resemble the first differential pressure generation device 46 depicted in FIG. 4, and discussed in detail below.

The air blocking member 16 can include any rigid, stretchable, and/or flexible material. In certain embodiments, the air blocking member 16 can include stainless steel, plastic, glass, silicone, cork, rubber, and/or a rubber-like material.

In one or more embodiments, the air blocking member 16 is shiftable relative to the shiftable plunger 18 and/or the extraction member 12. In the embodiment depicted in FIGS. 1a and 1b, the air blocking member 16 can slide along a vertical axis 13 relative to the extraction member 12 and the shiftable plunger 18, as depicted by the phantom position 16c of the air blocking member 16 in FIG. 1a. In various embodiments, the air blocking member 16 includes a handle 16b to aid a user in moving the air blocking member 16.

In certain embodiments, the air blocking member 16 is shiftable between an initial blocking position and a final extraction position. In the embodiment depicted in FIG. 1a, when the air blocking member 16 is shifted from an initial blocking position to a final extraction position, the lowermost surface 16a of the air blocking member 16 moves a total distance of $X_b$. In various embodiments, the air blocking member 16 entirely fills an internal chamber within the extraction member 12, such as, for example, the internal extraction chamber 12d of FIG. 1a, when the air blocking member 16 is in the initial blocking position. In one or more embodiments, the air blocking member 16 only partially fills an internal chamber within the extraction member 12 when the air blocking member 16 is in the initial blocking position.

In certain embodiments, the lowermost surface 16a of the air blocking member 16 is positioned at least 0.5$X_b$, 0.75 $X_b$, or 0.95 $X_b$ from the extraction inlet 12a when the air blocking member 16 is in the full extraction position. In one or more embodiments, the lowermost surface 16a of the air blocking member 16 is positioned less than 0.25 $X_b$, 0.15 $X_b$, 0.10 $X_b$, 0.05 $X_b$, or 0.01 $X_b$ from the extraction inlet 12a when the air blocking member 16 is in the initial blocking position. In one or more embodiments, the liquid extraction apparatus 10 has an $X_b$:$L_e$ ratio of at least 0.5:1, 0.75:1, or 0.95:1.

In certain embodiments, the air blocking member 16 is configured to create a pressure differential sufficient to draw a liquid from a container 11 into the extraction member 12 when the air blocking member 12 is shifted away from an initial blocking position toward a final extraction position. In one or more embodiments, moving the air blocking member 16 within the extraction member 12 can create at least a portion of a pressure differential between the extraction inlet 12a and the liquid storage inlet 14c, as further discussed below.

Returning now to the embodiment depicted in FIGS. 1a and 1b, the shiftable plunger 18 includes a base portion 18a and a handle portion 18b. In certain embodiments, at least a portion of the shiftable plunger 18 can be received inside the storage vessel 14. For example, the base portion 18a of the shiftable plunger 18 of FIG. 1a is received inside the storage vessel 14 and the handle portion 18b is partially received inside the storage vessel 14. In certain other embodiments, at least a portion of the shiftable plunger 18 can be located outside the storage vessel 14. In one or more embodiments, the shiftable plunger 18 can move, e.g., slide, relative to the storage vessel 14 along the vertical axis 13.

In certain embodiments, an interior channel 18i extends through at least a portion of the handle portion 18b, and through at least a portion of the base portion 18a, of the shiftable plunger 18. The interior channel 18i of FIG. 1a is substantially uniform in size. In certain other embodiments, the interior channel 18i is not substantially uniform in size. For example, in one or more embodiments, the portion of the interior channel 18i that extends through the base portion 18a (hereinafter referred to as interior channel portion 18e) can be substantially similar to the thickness of the air blocking member 16 received therein, while the portion of the interior channel 18i that extends through the handle portion 18b (hereinafter referred to as interior channel portion 18j) can be substantially larger than the thickness of the air blocking member 16 received therein.

In certain embodiments, the shiftable plunger 18 can include a sealing device 18f to block air and/or liquid from entering the interior channel portion 18e. In one or more embodiments, the sealing device 18f can be located anywhere in the interior channel portion 18e, or on any region of the base portion 18a of the shiftable plunger 18. In the embodiment depicted in FIG. 1b, the sealing device 18f can be located on the bottom surface 18h of the of the base portion 18a and circumferentially extend around the interior channel portion 18e to create a seal between the air blocking member 16 and the base portion 18a. In certain other embodiments where the interior channel portion 18j is larger than the thickness of the air blocking member 16, a seal device can be located on the top surface 18g of the base portion 18a and circumferentially extend around the interior channel portion 18e to create a seal between the air blocking member 16 and the top surface 18g of the shiftable plunger 18.

The sealing device 18f of FIGS. 1a and 1b can be any device that can form a seal to block air and/or liquid from entering the interior channel portion 18e. In certain embodiments, the sealing device 18f of FIGS. 1a and 1b can include an O-ring, a bushing, and/or a flexible material.

In certain other embodiments, an O-ring coupled to the air blocking member 16 can function as the sealing device 18f. For example, in such embodiments, the O-ring can be shaped such that when the air blocking member 16 is shifted upwards, the O-ring can contact the bottom surface 18h of the shiftable plunger 18 and block air and/or liquid from entering the interior channel portion 18e. Further, in such embodiments, once the O-ring is in contact with the bottom surface 18h, one can use the air blocking member 16 to move the shiftable plunger 18 upward.

In certain embodiments, the shiftable plunger 18 of FIG. 1a can be made of any material as long as the shiftable plunger 18 can create a pressure differential between the storage vessel 14 and the liquid in the container 11. In certain embodiments, the shiftable plunger 18 can be made of a rigid and/or a flexible material, such as, for example, glass, silicone, cork, rubber, rubber-like materials, plastic, and/or stainless steel. The shiftable plunger 18 of FIG. 1a includes at least two different materials, 18c and 18d. In one or more embodiments, the inner material 18c of the shiftable plunger 18 of FIG. 1a can include a rigid material, and the circumferentially extending outer material 18d can be a flexible material, e.g., an O-ring seal. In embodiments with a flexible outer material 18d, the outer material 18d can contact the inner surface 14a of the storage vessel 14 to form a seal between the air above the base portion 18a and the liquid below the base portion 18a of the shiftable plunger 18.

In certain embodiments, shifting the shiftable plunger 18 inside the storage vessel 14 can create a pressure differential between the extraction inlet 12a of the extraction member 12 and the liquid storage inlet 14c of the storage vessel 14, which can cause at least a portion of a liquid in the container 11 to flow from the container 11, through the extraction member 12, and into the storage vessel 14. In one or more embodiments, both the shifting of the air blocking member 16 and the shifting of the shiftable plunger 18 can create a pressure differential between the extraction inlet 12a of the extraction member 12 and the liquid storage inlet 14c of the storage vessel 14 to cause at least a portion of a liquid in the container 11 to flow from the container 11, through the extraction member 12, and into the storage vessel 14. For example, in one embodiment, first shifting the air blocking member 16 from an initial blocking position to a final extraction position, and then shifting the shiftable plunger 18 away from the liquid storage inlet 14c of the storage vessel 14 can cause at least a portion of a liquid in the container 11 to flow from the container 11, through the extraction member 12, and into the storage vessel 14. In certain embodiments, the air blocking member 16 and the shiftable plunger 18 can be shifted in substantially the same direction when creating a pressure differential between the extraction inlet 12a of the extraction member 12 and the liquid storage inlet 14c of the storage vessel 14.

In certain embodiments, to extract liquid from a container 11 using the liquid extraction apparatus 10 of FIG. 1a, one can insert the extraction member 12 into the container 11 so that the extraction inlet 12a is below the upper surface of the liquid in the container 11, such as, for example, by positioning the extraction inlet 12a at or near the bottom portion 11b of the container 11. In such embodiments, the lowermost surface 16a of the air blocking member 16 can be positioned at or near the extraction inlet 12a of the extraction member 12 to block at least a portion of air from the external environment from entering the extraction member 12 when the extraction member 12 initially contacts the liquid inside the container 11. Further, in such embodiments, the air blocking member 16 can be moved along the vertical axis 13 away from the extraction inlet 12a of the extraction member 12, creating at least a portion of a pressure differential between the extraction inlet 12a of the extraction member 12 and the liquid storage inlet 14c of the storage vessel 14. Additionally, in such embodiments, the shiftable plunger 18 can be moved along the vertical axis 13 away from the liquid storage inlet 14c to create at least a portion of a pressure differential between the extraction inlet 12a of the extraction member 12 and the liquid storage inlet 14c, which can cause at least a portion of a liquid in the container 11 to flow from the container 11, through the extraction member 12, and into the storage vessel 14. Furthermore, in such embodiments, when the shiftable plunger 18 is being shifted away from the extraction member 12, the air blocking member 16 can be positioned in the interior channel 18i away from the extraction member 12 so as not to block the flow of liquid from the container 11 and/or from the extraction member 12 into the storage vessel 14. In such embodiments, the shiftable plunger 18 also functions as a shiftable barrier with its bottom surface 18h contacting the liquid in the storage vessel 14, thereby blocking the air from the external environment from contacting the top surface of the liquid inside the storage vessel 14.

FIG. 1b depicts the liquid extraction apparatus 10 of FIG. 1a with the air blocking member 16 and the shiftable plunger 18 moved near the top portion 14b of the storage vessel 14. As discussed above with reference to FIG. 1a, in certain embodiments, when liquid has been extracted into the storage vessel 14, the air blocking member 16 and the shiftable plunger 18 can be positioned up and away from the extraction member 12 and/or the container 11.

In one or more embodiments not depicted in the figures, when liquid has been extracted from the container 11 using the liquid extraction apparatus 10, the apparatus 10 may be removed from engaging the container 11 and at least one sealing device may be used to seal the liquid inside the storage vessel 14. In such embodiments, a sealing device can be placed on the extraction inlet 12a of the extraction member 12 to seal the liquid inside the storage vessel 14. In embodiments where the extraction member 12 has been detached from the storage vessel 14, a sealing device may be positioned to seal the liquid storage inlet 14c of the storage vessel 14. The sealing device for the extraction inlet 12a or the liquid storage inlet 14c can be any conventional sealing device known in the art, such as, for example, a plug or a stopper. Additionally, in certain embodiments, the air blocking member 16 and/or the shiftable plunger 18 may be removed from the storage vessel 14, and a cap may be placed on the top end 14b of the storage vessel 14. The cap may be any suitable sealing device that can seal the top end 14b of the storage vessel 14 to prevent air and/or an external environment from contacting the liquid inside the storage vessel 14.

The liquid extraction apparatus 10 can also function to dispense liquid. For example, in certain embodiments, when a liquid has been stored in the storage vessel 14, the liquid can be dispensed through the extraction inlet 12a of the extraction member 12 and/or through the liquid storage inlet 14c of the storage vessel 14. In such embodiments, a particular amount of liquid, or all of the liquid, can be dispensed from the storage vessel 14 by moving the shiftable plunger 18 and/or the air blocking member 16 towards the liquid storage inlet 14c of the storage vessel 14. In certain other embodiments, the liquid can be dispensed through a pouring device in a cap positioned on the top portion 14b of the storage vessel 14.

Figure 2:
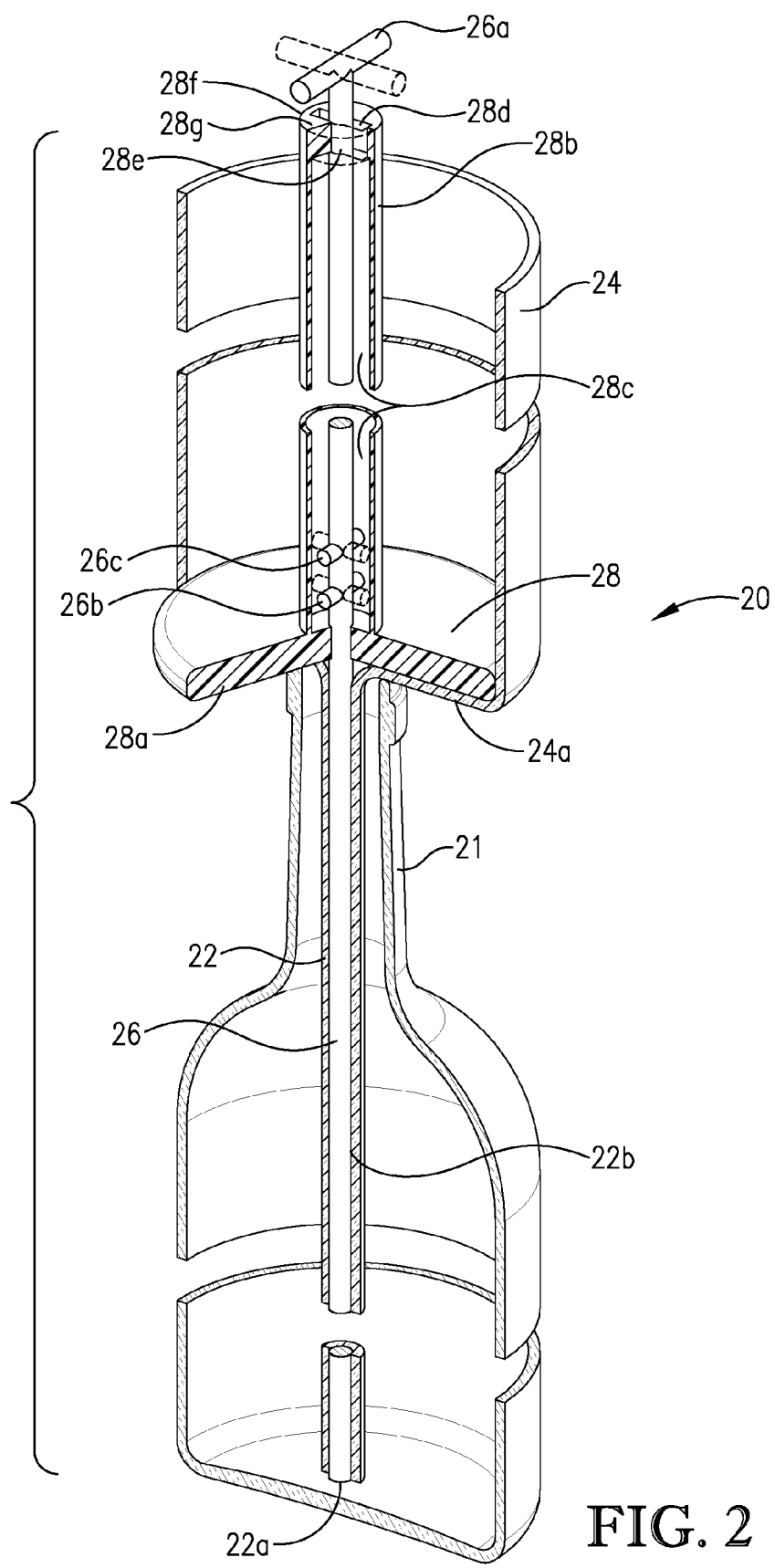
FIG. 2 is a perspective and cross-sectional view of a liquid extraction apparatus in accordance with another embodiment of the present invention, particularly illustrating a liquid extraction member partly received inside a container, a shiftable plunger partly received inside a storage vessel located above the container, and an air blocking member received inside both the extraction member and the shiftable plunger, where shiftable interlocking members extend outwardly from the air blocking member inside the interior channel of the shiftable plunger.

FIG. 2 depicts another embodiment of a liquid extraction apparatus 20 that includes an extraction member 22, a storage vessel 24, an air blocking member 26, and a shiftable plunger 28. In certain embodiments, the extraction member 22, the storage vessel 24, the air blocking member 26, and the shiftable plunger 28 can exhibit the same properties and characteristics as the respective components of the liquid extraction apparatus 10 of FIGS. 1a and 1b discussed above.

The air blocking member 26 of FIG. 2 includes two shiftable interlocking members 26b and 26c. In the embodiment depicted in FIG. 2, the shiftable interlocking members 26b and 26c each include two protrusions extending away from the air blocking member 26 in opposite directions. In certain embodiments, as that depicted in FIG. 2, the interlocking members 26b and 26c can extend from the air blocking member 26 in directions substantially parallel to one another. In certain other embodiments, the interlocking members 26b and 26c can extend from the air blocking member 26 in directions substantially perpendicular to one another. In one or more embodiments, the liquid extraction apparatus 20 can include one shiftable interlocking member 26b or 26c.

In various embodiments, where the liquid extraction apparatus 20 has one, two, or more shiftable interlocking members 26b and/or 26c, the air blocking member 26 can be shifted between a locked configuration, where at least one shiftable interlocking member 26b and/or 26c is used to selectively lock the air blocking member 26 to the shiftable plunger 28 such that movement of one of the air blocking member 26 and the shiftable plunger 28 causes movement of the other of the air blocking member 26 and the shiftable plunger 28, and an unlocked configuration, where the air blocking member 26 and the shiftable plunger 28 are unlocked to permit movement of the air blocking member 26 relative to the shiftable plunger 28.

Referring now to the embodiment depicted in FIG. 2, in the unlocked configuration, the air blocking member 26 is positioned so that the protrusions 26b and 26c can move, e.g., slide, inside the interior channel 28c of the shiftable plunger 28 and through the opening 28d at the top end 28f of the handle portion 28b. The phantom lines in FIG. 2 indicate the position of the handle 26a and the interlocking members 26b and 26c when the air blocking member 26 is in the unlocked configuration. In the locked configuration, not depicted in FIG. 2, the air blocking member 26 is positioned so that at least one of the interlocking members 26b and/or 26c cannot slide through the opening 28d on the top end 28f of the handle portion 28b without rotating the handle 26a to re-position the interlocking members 26b and/or 26c to align with the opening 28d. The opening 28d, the handle portion 28b, and the interlocking members 26b and 26c can be any shape or size as long as the air blocking member 26 can be shifted between a locked configuration and an unlocked configuration.

In certain embodiments, to extract a liquid from a container 21 using the liquid extraction apparatus 20 of FIG. 2, the air blocking member 26 can be shifted away from the extraction inlet 22a of the liquid extraction member 22, to a position where interlocking member 26c is above the opening 28d and interlocking member 26b is below the opening 28d, thereby creating a pressure differential between the extraction inlet 22a and the internal extraction chamber 22b of the extraction member 22, thereby causing liquid to flow into the internal extraction chamber 22b. In such embodiments, when the interlocking members 26b and 26c are in the aforementioned position, the air blocking member 26 can be positioned so that the interlocking member 26b is contacting the underside 28e of the top end 28f of the handle portion 28b, e.g., by shifting the handle 26a so that the interlocking member 26b cannot slide through the opening 28d, thereby shifting the air blocking member 26 into the locked configuration. In such embodiments, once in the locked configuration, continued movement of the air blocking member 26 away from the extraction inlet 22a causes the shiftable plunger 28 to also move in the same direction, thereby causing the liquid to flow from the container 21 and/or the internal extraction chamber 22b into the storage vessel 24. To dispense wine stored in the storage vessel 24 when the air blocking member 26 is in the locked configuration, the interlocking member 26c can contact the topside 28g of the top end 28f of the handle portion 28b so that movement of the air blocking member 26 toward the extraction member 22 causes the shiftable plunger 28 to also move in that direction, thereby causing liquid to flow out of the extraction inlet 22a. Further, in such embodiments, once the shiftable plunger 28 has been moved so that the bottom portion 28a is in contact with the bottom portion 24a of the storage vessel 24, the air blocking member 26 can be shifted to the independently movable configuration, e.g., by shifting the handle 26a so that the interlocking member 26c can slide through opening 28d and into the interior channel 28c. In such embodiments, once in the independently movable configuration, the air blocking member 26 can be moved towards the bottom end 22a of the extraction member 22 to dispense the liquid remaining therein.

In certain embodiments, where the interlocking members 26b and 26c extend from the air blocking member 26 in directions substantially perpendicular to one another, the liquid extraction apparatus 20 can still perform the liquid extraction procedure discussed above. However, in such embodiments, one skilled in the art can rotate the air blocking member 26 as necessary to shift between the locked and unlocked configurations.

In embodiments where the air blocking member 26 only includes one interlocking member 26b or 26c, the liquid extraction apparatus 20 can still perform the liquid extraction procedure discussed above with reference to two interlocking members 26b and 26c. However, in such embodiments, the single interlocking member 26b or 26c will need to separately interlock with the underside 28e and the top side 28g of the shiftable plunger 28 in order to move the shiftable plunger up and down, respectively.

Figure 3:
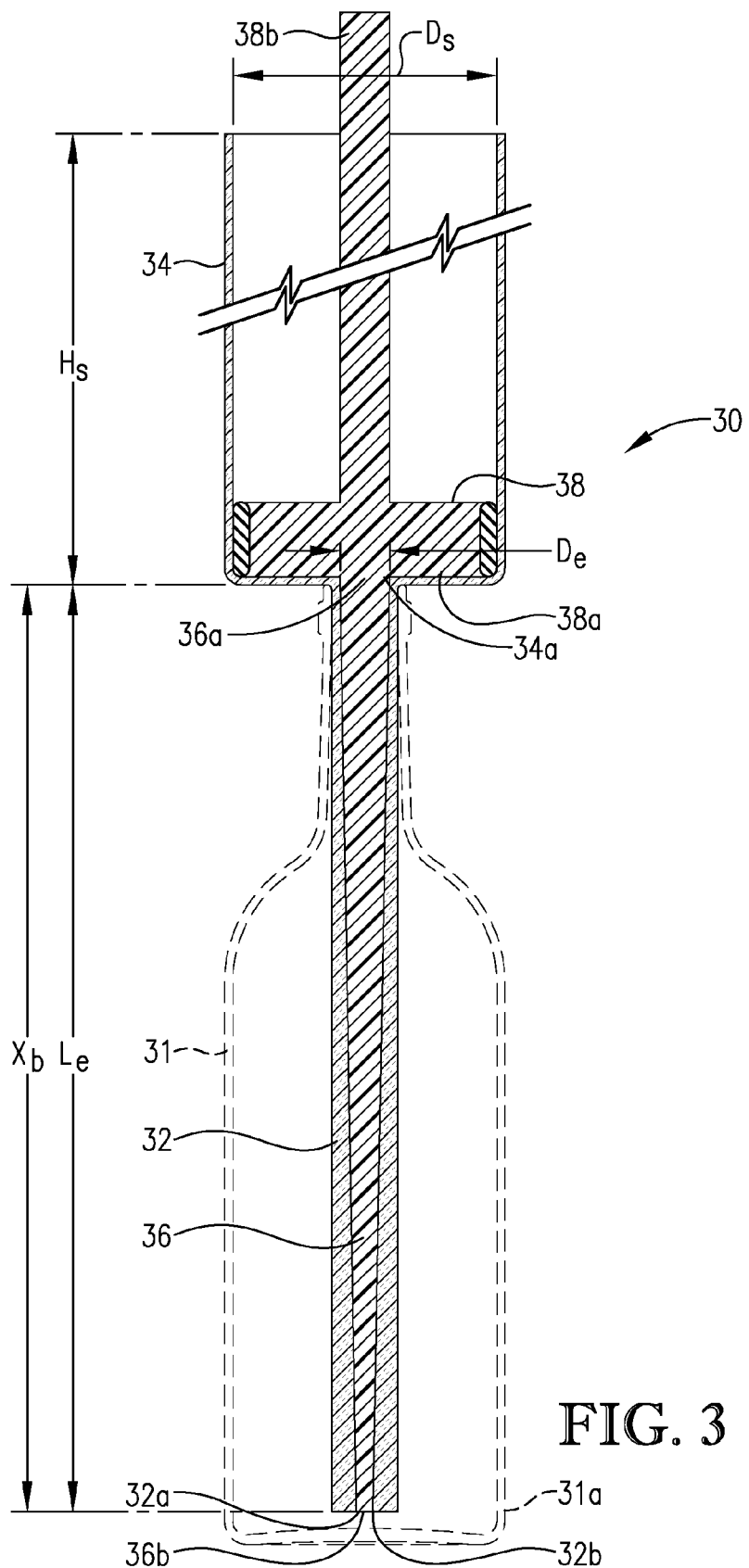
FIG. 3 is a cross-sectional view of a liquid extraction apparatus in accordance with yet another embodiment of the present invention, particularly illustrating an air blocking member and a liquid extraction member partly received inside a container, and a shiftable plunger partly received inside a storage vessel located above the container, where the air blocking member and the shiftable plunger are integrally connected.

FIG. 3 depicts another embodiment of a liquid extraction apparatus 30 in accordance with the present invention. The liquid extraction apparatus 30 of FIG. 3 includes a storage vessel 34, a liquid extraction member 32, an air blocking member 36, and a shiftable plunger 38. In certain embodiments, the extraction member 32 and the storage vessel 34 can have the same characteristics and parameters as the extraction member 12 and storage vessel 14 discussed above with reference to FIGS. 1a and 1b.

In certain embodiments, the air blocking member 36 can be fixedly attached to the shiftable plunger 38. For example, in the embodiment depicted in FIG. 3, the base portion 38a and the handle portion 38b of the shiftable plunger 38 are composed of one single article that is integral to the air blocking member 36. The air blocking member 36 and the shiftable plunger 38 can be made of the same materials as the air blocking member 16 and shiftable plunger 18 discussed above with reference to FIGS. 1a and 1b.

In an embodiment not depicted in the figures, the air blocking member 36 and the shiftable plunger 38 can be separate articles and fixedly attached to one another. In such embodiments, any attachment mechanism can be used to attach the top end 36a of the air blocking member 36 to the base portion 38a of the shiftable plunger 38, such as, for example, by complementary threaded portions. Further, in such embodiments, when the apparatus 30 is not in use, the air blocking member 36 can be detached from the shiftable plunger 38 for more compact storage and/or easier cleaning.

In the embodiment depicted in FIG. 3, the air blocking member 36 is tapered so as to become narrower toward the lowermost surface 36b. For example, the air blocking member 36 of FIG. 3 has a tapered profile so that the maximal cross sectional area $A_1$ of the top end 36a is greater than the maximal cross sectional area $A_2$ of the lowermost surface 36b. In one or more embodiments, the air blocking member 36 of FIG. 3 can have a length $L_a$ of at least 5 inches, 7 inches, or 9 inches, and/or not more than 48 inches, 28 inches, or 20 inches.

The extraction member 32 of FIG. 3 has an internal extraction chamber 32b that is complimentary in shape to the tapered profile of the air blocking member 36, so that the air blocking member 36 can be entirely or partially received inside the extraction member 32. In one or more embodiments, the extraction member 32 and air blocking member 36 can be any complimentary shape and size as long as both members 32 and 36 can be inserted into a container 31 and reach to or near the bottom portion 31a of the container 31. In the embodiment depicted in FIG. 3, the air blocking member 36 can move relative to the extraction member 32 such as, for example, by shifting the shiftable plunger 38.

In certain embodiments, the air blocking member 36 is shiftable between an initial blocking position and a final extraction position. In the embodiment depicted in FIG. 3, when the air blocking member 36 is shifted from an initial blocking position to a final extraction position, the lowermost surface 36b of the air blocking member 36 moves a total distance of $X_b$. In various embodiments, when the air blocking member 36 is in the initial blocking position, the air blocking member 36 entirely fills the internal extraction chamber 32b within the extraction member 32. In one or more embodiments, when the air blocking member 16 is in the initial blocking position, the air blocking member 36 partially fills the internal extraction chamber 32b within the extraction member 32.

In certain embodiments, the lowermost surface 36b is positioned at least $0.5X_b$, $0.75 X_b$, or $0.95 X_b$ from the extraction inlet 32a when the air blocking member 36 is in the full extraction position. In one or more embodiments, the lowermost surface 36a is positioned less than $0.15 X_b$, $0.10 X_b$, $0.05 X_b$, or $0.01 X_b$ from the extraction inlet 32a when the air blocking member 36 is in the initial blocking position. In certain embodiments, the extraction apparatus 30 has an $X_b{:}L_e$ ratio of at least 0.5:1, 0.75:1, or 0.95:1.

In certain embodiments, to extract a liquid from the container 31, the extraction member 32 can be inserted into the container 31 so that the extraction inlet 32a is positioned below the surface of the liquid in the container 31. In such embodiments, the air blocking member 36 can be shifted into the initial blocking position before the extraction member 32 is inserted into the container 31 so as to block at least a portion of air and/or liquid from entering the extraction chamber 32b. Further, in such embodiments, shifting the shiftable plunger 38 located inside the storage vessel 34 can cause the air blocking member 36 to shift from the initial blocking position to the final extraction position, and also create a pressure differential between the extraction inlet 32a and the liquid storage inlet 34a causing the liquid to flow through the extraction member 32 and into the storage vessel 34. Additionally, in such embodiments, one can use the handle portion 38b to shift the shiftable plunger 38. In such embodiments, when the lowermost surface 36b of the air blocking member 36 is moved away from the extraction inlet 32a, a gap is created between at least a portion of the air blocking member 36 and the internal extraction chamber 32b, thereby allowing the liquid to flow into the extraction member 32 and on into the storage vessel 34.

Figure 4:
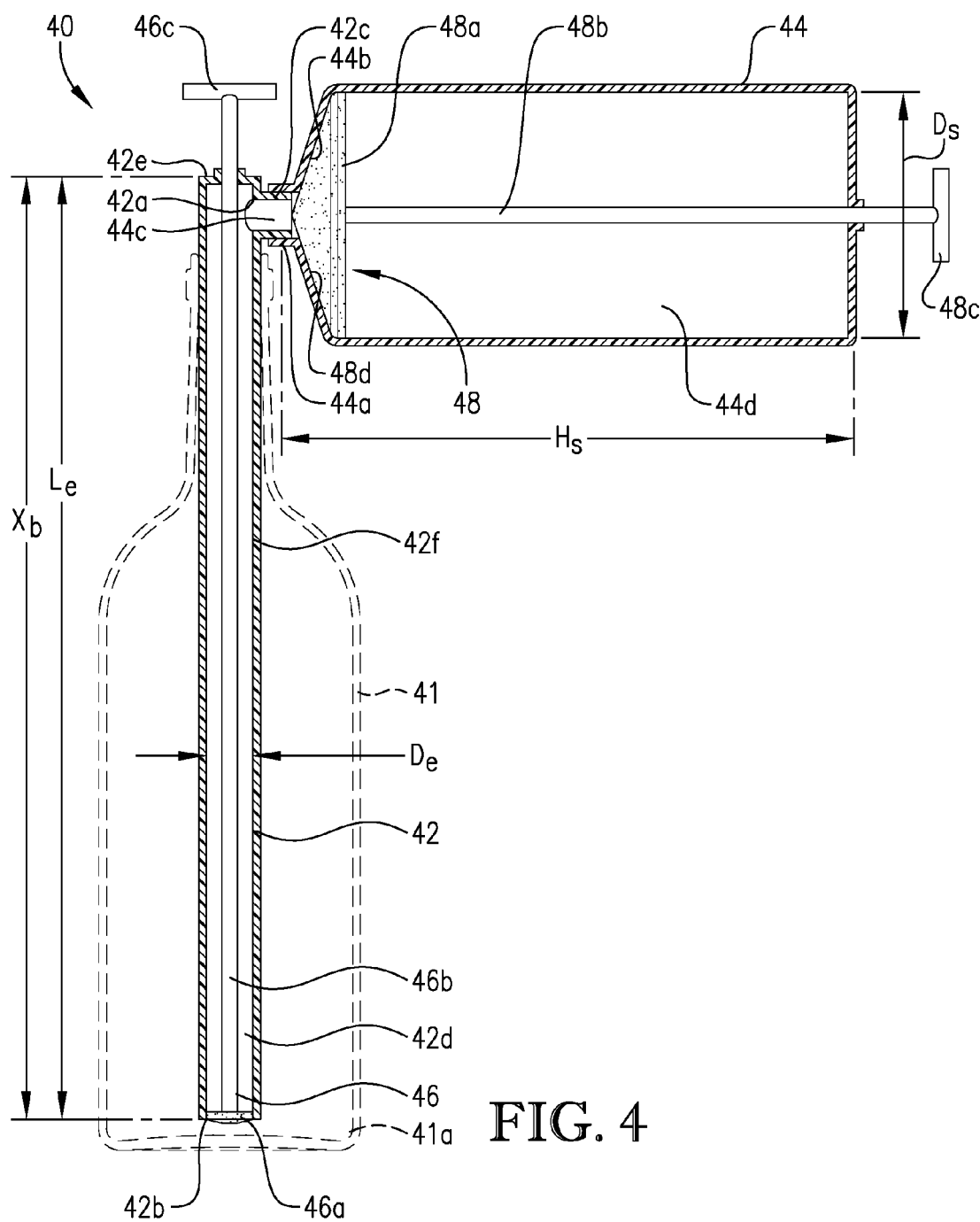
FIG. 4 is a cross-sectional and side view of a liquid extraction apparatus in accordance with another embodiment of the present invention, particularly illustrating a first differential pressure generation device and a liquid extraction member partly received inside a container, and a second differential pressure generation device partly received inside a storage vessel, with the storage vessel attached to the top portion of the extraction member in a perpendicular orientation.

FIG. 4 depicts another embodiment of a liquid extraction apparatus 40 in accordance with the present invention. The liquid extraction apparatus 40 can be used on any liquids or any containers, such as, for example, the liquids and containers discussed with reference to the liquid extraction apparatus 10 of FIGS. 1a and 1b. In certain embodiments, the container 41 is a wine bottle and the liquid is wine. The liquid extraction apparatus 40 of FIG. 4 includes an extraction member 42 with at least a portion of a first differential pressure generation device 46 received therein, and a storage vessel 44 with at least a portion of a second differential pressure generation device 48 received therein.

In certain embodiments, the first differential pressure generation device 46 and the second differential pressure generation device 48 are both plungers shiftably disposed in the extraction member 42 and the storage vessel 44, respectively. For example, in the embodiment depicted in FIG. 4, the first pressure differential generation device 46 is a plunger shiftably disposed in the extraction member 42. In addition, the second differential pressure generation device 48 of the embodiment depicted in FIG. 4 is a plunger shiftably disposed in the storage vessel 44. The first and second pressure differential generation devices 46 and 48, respectively, can be any device that is able to generate a pressure differential between the liquid extraction apparatus 40 and a container 41, and a specific device can be chosen by one skilled in the art for a particular purpose. In one or more embodiments, the first pressure differential generation device 46 is a vacuum pump coupled in fluid flow communication with the extraction member 42. In certain other embodiments, the first differential pressure generation device 46 is a compression pump configured to attach to the container 41. In yet another embodiment, the second differential pressure generation device 48 can be a vacuum pump coupled in fluid flow communication with the storage vessel 44. The additional embodiments of differential pressure generation devices, e.g., the compression pump and the vacuum pump, are further discussed below with respect to FIG. 5.

In certain embodiments, the extraction member 42 and the first differential pressure generation device 46 can have the same properties and characteristics of the extraction member 12 and the air blocking member 16, respectively, discussed above with reference to FIGS. 1a and 1b. For example, the extraction member 42 and the first differential pressure generation device 46 can have the same $L_e$ and $X_b$ values and ratios as those of the extraction member 12 and the air blocking member 16, respectively, detailed above with reference to FIGS. 1a and 1b.

In certain embodiments, the first differential pressure generation device 46 can include a shaft 46b with an air blocking device 46a and a handle 46c at opposing ends thereof. The air blocking device 46a can include any flexible or rigid material that can generate a pressure differential between the extraction apparatus 40 and the liquid to be extracted from the container 41 and/or block air from contacting the liquid as the liquid enters the interior extraction chamber 42d of the extraction member 42. In one or more embodiments, the cross sectional area of the shaft 46b can be large enough to block air and/or liquid from entering the interior extraction chamber 42d of the extraction member 42 in the absence of an air blocking device 46a.

In the embodiment depicted in FIG. 4, the second differential pressure generation device 48 includes a shaft 48b with a base portion 48a and a handle 48c at opposing ends thereof. In one or more embodiments, the base portion 48a can include any flexible or rigid material that is capable of creating a pressure differential so as to draw liquid into the storage vessel 44 from the extraction member 42 and/or the container 41. To aid in creating a pressure differential between the storage vessel 44 and the extraction member 42 and/or the container 41, the base portion 48a of FIG. 4 may include a tapered profile 48d extending toward the complimentary shaped tapered portion 44b of the storage vessel 44. In another embodiment, an air blocking protrusion can be attached to the base portion 48a of the second differential pressure generation device 48 in order to block air and/or liquid from entering into the storage vessel 44 via the through opening 44c. In such embodiments, the air blocking protrusion can be any material that is capable of blocking air and/or liquid from entering into the storage vessel 44, such as, for example, silicone, rubber, and/or a rubber-like material.

The storage vessel 44 can have the same properties and characteristics as those of the storage vessel 14 discussed above with reference to FIGS. 1a and 1b. For example, the storage vessel 44 can have the same $D_s$ and $H_s$ values and ratios as those described above with respect the storage vessel 14 of FIGS. 1a and 1b. In certain embodiments, such as that depicted in FIG. 4, the storage vessel 44 and the extraction member 42 extend substantially perpendicular to one another. In certain other embodiments, the storage vessel 44 can be oriented at any other position or angle relative to the extraction member 42, and a particular position or angle can be chosen by one skilled in the art for a specific purpose.

In the embodiment depicted in FIG. 4, the extraction member 42 is coupled in fluid flow communication with the storage vessel 44. In certain embodiments, the extraction member 42 includes a connection member 42c that can connect to the connection member 44a of the storage vessel 44. The connection member 42c can be located on any portion of the extraction member 42, but is preferably in a location, such as near the upper portion 42e of the extraction member 42, where the storage vessel 44 can remain connected to the extraction member 42 when the extraction member 42 is inserted into a container 41 with the extraction inlet 42b of the extraction member 42 positioned at or near the bottom portion 41a of the container 41. In the embodiment depicted in FIG. 4, the connection member 42c extends from a sidewall 42f near the upper portion 42e of the extraction member 42. In one or more embodiments, the connection member 42c does not extend outwardly from the extraction member 42. The connection members 42c and 44a can include any type of connection device or mechanism as long as there is a through-opening 44c for a liquid to flow from the extraction member 42 into the storage vessel 44. For example, in certain embodiments, the connection members 42c and 44a can be connected by complimentary threaded portions.

In certain embodiments, the liquid extraction apparatus 40 of FIG. 4 can extract a liquid from the container 41 by inserting the extraction member 42 into the container 41 with the extraction inlet 42b positioned below the surface of the liquid in the container 41. In one or more embodiments, the air blocking device 46a can be positioned at or near the extraction inlet 42b when the extraction member 42 is inserted into the liquid inside the container 41, to thereby block at least a portion of air and/or liquid from entering the interior extraction chamber 42d. Further, in certain embodiments, a first pressure differential can be created between the extraction inlet 42b and the upper portion 42e of the extraction member 42 so as to cause liquid to flow from the container 41 up into the upper portion 42e of the extraction member 42. In one or more embodiments a plunger disposed in the extraction member 42 can be used to fully, or at least partly, create the first pressure differential. In certain embodiments, a second pressure differential can be created between the upper extraction outlet 42a of the extraction member 42 and the interior 44d of the storage vessel 44 to cause at least a portion of the liquid to flow from the extraction member 42, through the upper extraction outlet 42a, and into the storage vessel 44. Furthermore, in one or more embodiments, a plunger disposed in the storage vessel 44, and/or a vacuum pump connected in fluid flow communication with the storage vessel 44, can be used to create the second pressure differential. In certain other embodiments, plungers disposed in the extraction member 42 and the storage vessel 44, respectively, can be used to create both the first and second pressure differentials. In embodiments where a plunger is used to create the first pressure differential, the air blocking member 46 can effectively function as the plunger. In such embodiments, when the liquid is extracted into the extraction member 42, the air blocking device 46a can be positioned above the extraction outlet 42a so that the second differential pressure generation device 48 can create the second pressure differential and cause the liquid to flow from the extraction member 42 into the storage vessel 44.

In certain embodiments, once the liquid has been extracted into the storage vessel 44, the storage vessel 44 can be removed from the extraction member 42 by disconnecting the connection members 42c and 44a. In such embodiments, the base portion 48a of the second differential pressure generation device 48 can function as a barrier to block a surface of the liquid from contacting the air. Additionally, in such embodiments, a seal device may be placed into or onto connecting member 44a to block air from contacting the liquid and/or to block the liquid from exiting the storage vessel 44. Any type of common seal device can be used, such as, for example, a rubber or silicone stopper or plug. Further, in such embodiments, to dispense the liquid stored in the storage vessel 44, the base portion 48a of second differential pressure generation device 48 can be moved toward the connecting member 44a to force the liquid out through the through-opening 44c. Alternatively, in such embodiments, the storage vessel 44 can be reconnected to the extraction member 42 and the liquid can be dispensed through the extraction inlet 42b of the extraction member 42 by positioning the air blocking device 46a above the connection member 42c and moving the base portion 48a of the second differential pressure generation device 48 towards the upper extraction outlet 42a. Alternatively, in such embodiments, the second differential pressure generation device 48 can be removed from the storage vessel 44 and the liquid can be poured from the storage vessel 44.

Figure 5:
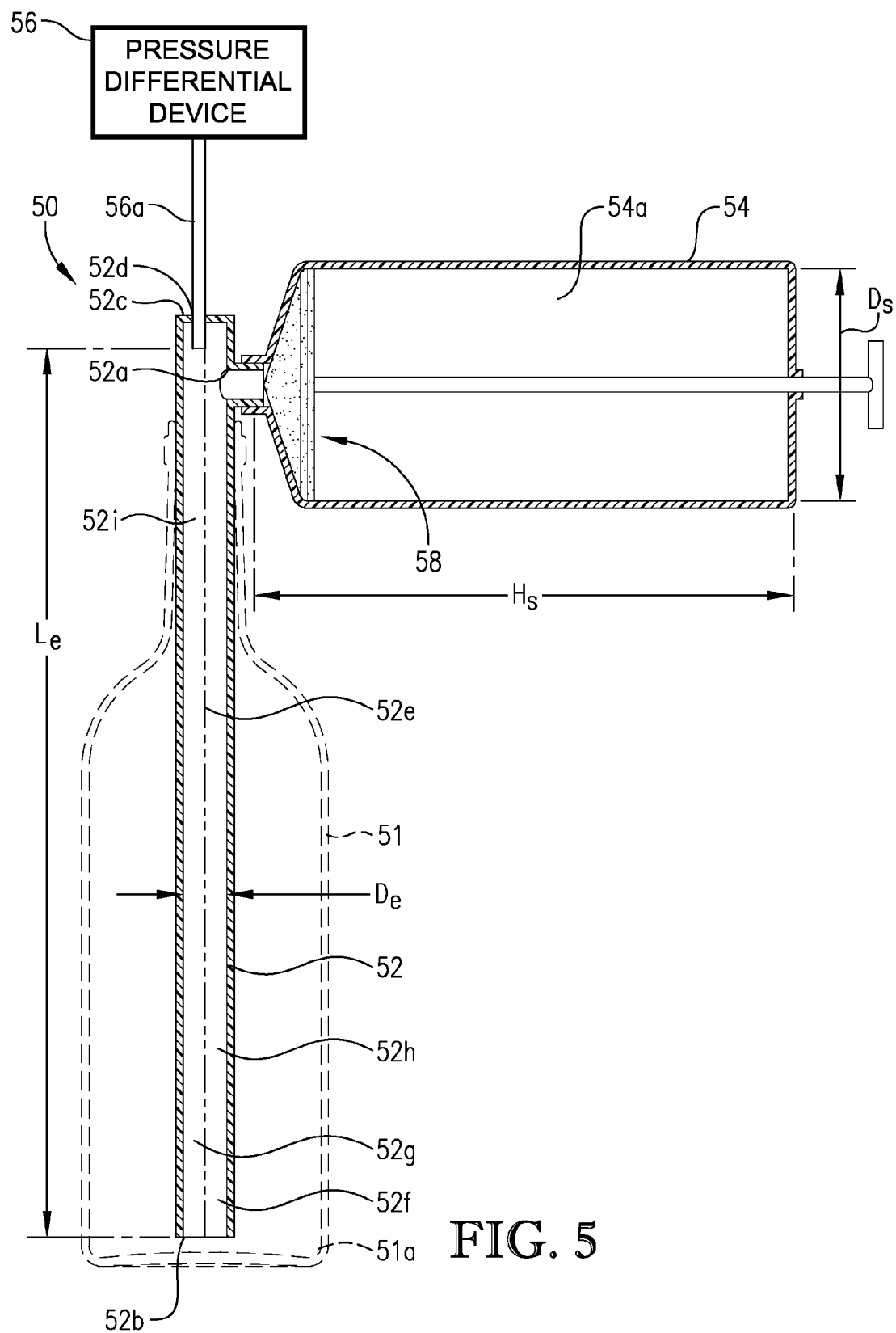
FIG. 5 is a cross-sectional and side view of a liquid extraction apparatus in accordance with another embodiment of the present invention, particularly illustrating a first differential pressure generation device coupled to a liquid extraction member that is partly received inside a container, and a second differential pressure generation device partly received inside a storage vessel, with the storage vessel attached to the top portion of the extraction member in a perpendicular orientation.

FIG. 5 depicts another embodiment of a liquid extraction apparatus 50 in accordance with the present invention. The liquid extraction apparatus 50 can be used on any liquids or any containers, such as, for example, the liquids and containers discussed above with reference to the liquid extraction apparatus 10 of FIGS. 1a and 1b. In certain embodiments, the container 51 is a wine bottle and the liquid is wine.

The liquid extraction apparatus 50 of FIG. 5 includes an extraction member 52 coupled to a first differential pressure generation device 56, and a storage vessel 54 with at least a portion of a second differential pressure generation device 58 received therein. In certain embodiments, the extraction member 52 and the storage vessel 54 can have the same properties, and shape and size characteristics, as the extraction member 42 and the storage vessel 44, respectively, discussed above with respect to FIG. 4. In one or more embodiments, the second differential pressure generation device 58 can have the same properties, and shape and size characteristics, as the second differential pressure generation device 48 discussed above with reference to FIG. 4.

In certain embodiments, the first differential pressure generation device 56 of FIG. 5 can be a vacuum pump coupled in fluid flow communication with the extraction member 52. In the embodiment depicted in FIG. 5, the first differential pressure generation device 56 is coupled at the top end 52c of the extraction member 52 via an opening 52d. A portion 56a of the first differential pressure generation device 56 can be inserted into the opening 52d. In certain embodiments, a sealing device can be used to secure the portion 56a of the first differential pressure generation device 56 into the opening 52d, such as, for example, by using an O-ring. Any sealing device can be used and a particular sealing device be chosen by one skilled in the art.

In certain embodiments, to extract a liquid from the container 51, a first differential pressure generation device 56, such as, for example, a vacuum pump, can create a pressure differential between the extraction inlet 52b and the upper portion 52i of the extraction member 52, thereby causing at least a portion of the liquid in the container 51 to flow from the container 51 into the upper portion 52i of the extraction member 52. In such embodiments, a second differential pressure generation device 58 can create a pressure differential between the extraction outlet 52a in the upper portion 52i of the extraction member 52 and the interior 54a of the storage vessel 54, thereby causing at least a portion of the liquid to flow from the extraction member 52, through the extraction outlet 52a, and into the storage vessel 54.

In one or more embodiments, the first differential pressure generation device 56 can be a compression pump configured to provide a pressurized gas to the interior of the container 51, and configured to create a pressure differential between the extraction inlet 52b and the upper portion 52i of the extraction member 52. The pressurized gas may be air or any inert gas, such as, for example, nitrogen or argon. In such embodiments, the extraction member 52 can include a septum, shown as a phantom line 52e, that separates the interior 52f of the extraction member 52 into a first interior portion 52g and a second interior portion 52h. In such embodiments, the pressurized gas can enter into the first interior portion 52g and cause the liquid in the container 51 to flow up into the second interior portion 52h, though the extraction outlet 52a and into the storage vessel 54. In such embodiments, when the second differential pressure generation device 58 is a plunger, the liquid flowing into the storage vessel 54 can cause the plunger to move away from the extraction outlet 52a, and/or the plunger can be positioned a sufficient distance away from the extraction outlet 52a to provide space for the liquid to flow into the storage vessel 54. In certain other embodiments, the second differential pressure generation device 58 can at least partly cause the liquid to flow from the container 51 and/or the extraction member 52 into the storage vessel 54.

In certain embodiments, once the liquid has been extracted into the storage vessel 54, any or all of the processes and structures regarding the storing and dispensing of the liquid, discussed above with reference to the apparatus 40 of FIG. 4, can be used with the apparatus 50 of FIG. 5.

In certain embodiments, the process of extracting liquid from a container using any of the liquid extraction apparatuses, e.g., liquid extraction apparatuses 10, 20, 30, 40, and/or 50 of the present invention, may be performed manually and/or automatically with a machine.

In one or more embodiments, any of the liquid extraction apparatuses of the present invention, e.g., liquid extraction apparatuses 10, 20, 30, 40, and/or 50, may include a housing structure to conceal all or a portion of the apparatus. In such embodiments, for example, the entire apparatus may be received inside a housing structure to store the apparatus when not in use. In one or more embodiments that include a housing structure, the housing structure may include shelves, hanging devices, and/or stands to hold at least one or more components of any of the liquid extraction apparatuses contemplated by this invention.

It is the inventor's intent to rely on the Doctrine of Equivalents to determine and assess the reasonably fair scope of the present invention as it pertains to any processes and systems not materially departing from but outside the literal scope of the invention as set forth in the following claims.

What is claimed is:

1. An apparatus for extracting a liquid from a container having an opening, said apparatus comprising:
   a liquid extraction member having a length ($L_e$) of at least 2 inches, wherein one end of said extraction member includes a liquid extraction inlet, wherein said extraction member is configured for insertion through said opening of said container and for positioning of said extraction inlet below the surface of said liquid,
   a storage vessel defining a liquid storage inlet coupled in fluid flow communication with said extraction member, wherein the maximum internal diameter ($D_s$) of said storage vessel is greater than the maximum internal diameter ($D_e$) of said liquid extraction member, wherein said storage vessel has a maximum height ($H_s$), and wherein said apparatus has an $L_e$:$H_s$ ratio of at least 1:1;
   a shiftable plunger received in said storage vessel and operable to create a pressure differential between said storage inlet and said extraction inlet so as to draw said liquid from said container, through said extraction member, and into said storage vessel; and
   an air blocking member received in said extraction member and shiftable between an initial blocking position and a final extraction position, wherein said air blocking member presents a lowermost surface that moves through a total distance ($X_b$) as said air blocking member is shifted from said initial blocking position to said final extraction position, wherein said lowermost surface is positioned less than 0.25$X_b$ from said extraction inlet when said air blocking member is in said initial blocking position,
   wherein said liquid extraction member and said storage vessel extend substantially perpendicular to one another, said air blocking member and said shiftable plunger are separately moveable, and said storage vessel is detachably connected to said liquid extraction member at an end of the liquid extraction member opposite said liquid extraction inlet.

2. The apparatus according to claim 1, wherein $D_e$ is at least 0.1 inches and not more than 4 inches.

3. The apparatus according to claim 1, wherein $L_e$ is at least 4 inches and not more than 40 inches, wherein the $L_e$:$H_s$ ratio is not more than 5:1.

4. The apparatus according to claim 1, wherein said apparatus has an $X_b$:$L_e$ ratio of at least 0.5:1.

5. The apparatus according to claim 1, wherein $D_e$ is at least 0.1 inches and not more than 4 inches, wherein $L_e$ is at least 4 inches and not more than 40 inches, wherein the $L_e$:$H_s$ ratio is not more than 5:1.

6. The apparatus according to claim 1, wherein said container is a wine bottle and said liquid is wine.

7. The apparatus according to claim 6, wherein $D_e$ is at least 0.1 inches and not more than 4 inches.

8. The apparatus according to claim 6, wherein $L_e$ is at least 4 inches and not more than 40 inches, wherein the $L_e$:$H_s$ ratio is not more than 5:1.

9. The apparatus according to claim 1, wherein said air blocking member is shiftable relative to said plunger, wherein said air blocking member is configured to create a pressure differential sufficient to draw said liquid into said extraction member when said air blocking member is shifted away from said initial blocking position toward said full extraction position.

10. The apparatus according to claim 9, wherein said container is a wine bottle and said liquid is wine.

11. The apparatus according to claim 1, wherein said air blocking member is tapered so as to become narrower towards said lowermost surface.

12. A process for extracting a liquid from a container and storing said liquid, said process comprising the steps of:
   (a) inserting a liquid extraction member having a length ($L_e$) of at least 2 inches into a container to a depth such that a liquid extraction inlet of said extraction member extends below the surface of said liquid received in said container;
   (b) creating a pressure differential between said extraction inlet and a storage inlet of a storage vessel by displacing a shiftable plunger to thereby cause at least a portion of said liquid to flow from said container, through said extraction member, and into said storage vessel, wherein the maximum internal diameter ($D_s$) of said storage vessel is greater than the maximum internal diameter ($D_e$) of said liquid extraction member, wherein said storage vessel has a maximum height ($H_s$), and wherein an $L_e$:$H_s$ ratio is at least 1:1; and
   (c) during at least a portion of step (b), shifting an air blocking member in said liquid extraction member from an initial blocking position to a final extraction position, wherein said air blocking member presents a lowermost surface that moves through a total distance ($X_b$) as said air blocking member is shifted from said initial blocking position to said final extraction position, wherein said lowermost surface is positioned less than 0.25$X_b$ from said extraction inlet when said air blocking member is in said initial blocking position, wherein said liquid extraction member and said storage vessel extend substantially perpendicular to one another, said air blocking member and said shiftable plunger are separately moveable, and said storage vessel is detachably connected to said liquid extraction member at an end of the liquid extraction member opposite said liquid extraction inlet.

13. The process according to claim 12, wherein $D_e$ is at least 0.1 inches and not more than 4 inches.

14. The process according to claim 12, wherein $L_e$ is at least 4 inches and not more than 40 inches, wherein the $L_e$:$H_s$ is not more than 5:1.

15. The process according to claim 12, wherein $D_e$ is at least 0.1 inches and not more than 4 inches, wherein $L_e$ is at least 4 inches and not more than 40 inches, wherein the $L_e$:$H_s$ is not more than 5:1.

16. The process according to claim 12, wherein said container is a wine bottle and said liquid is wine.

17. The process according to claim 16, wherein $D_e$ is at least 0.1 inches and not more than 4 inches.

18. The process according to claim 16, wherein $L_e$ is at least 4 inches and not more than 40 inches, wherein the $L_e$:$H_s$ ratio is not more than 5:1.

19. The process according to claim 12, wherein step (b) includes first shifting said air blocking member from said initial blocking position to said final extraction position and then shifting said plunger away from said inlet of said storage vessel.

20. The process according to claim 19, wherein said container is a wine bottle and said liquid is wine.

* * * * *